(12) United States Patent
Liu et al.

(10) Patent No.: US 10,823,652 B2
(45) Date of Patent: Nov. 3, 2020

(54) TRIAXIAL HIGH TEMPERATURE AND HIGH PRESSURE ROCK MECHANICS LOAD TEST PLATFORM

(71) Applicant: Sichuan University, Chengdu (CN)

(72) Inventors: Jianfeng Liu, Chengdu (CN); Xiaozhang Lei, Chengdu (CN); Wenxi Fu, Chengdu (CN); Feng Dai, Chengdu (CN); Yufeng Wei, Chengdu (CN); Chunping Wang, Chengdu (CN); Huining Xu, Chengdu (CN); Jianliang Pei, Chengdu (CN); Fei Wu, Chengdu (CN); Gang Chen, Chengdu (CN); Jinbing Wei, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 23 days.

(21) Appl. No.: 16/396,797

(22) Filed: Apr. 29, 2019

(65) Prior Publication Data

US 2019/0331568 A1   Oct. 31, 2019

(30) Foreign Application Priority Data

Apr. 28, 2018 (CN) .......................... 2018 1 0403196

(51) Int. Cl.
*G01N 3/18* (2006.01)
*G01N 33/24* (2006.01)
*G01N 3/02* (2006.01)
*G01N 3/06* (2006.01)
*G01L 5/00* (2006.01)
*G01N 3/10* (2006.01)

(52) U.S. Cl.
CPC .............. *G01N 3/06* (2013.01); *G01L 5/0028* (2013.01); *G01N 3/10* (2013.01); *G01N 2203/0048* (2013.01); *G01N 2203/0226* (2013.01); *G01N 2203/0232* (2013.01); *G01N 2203/0256* (2013.01); *G01N 2203/0676* (2013.01); *G01N 2203/0694* (2013.01)

(58) Field of Classification Search
CPC ... G01N 2203/0048; G01N 2203/0605; G01N 2203/0256; G01N 3/18; G01N 3/062; F16C 19/10; F16C 35/06; F16C 2240/06
See application file for complete search history.

(56) References Cited

U.S. PATENT DOCUMENTS 7,143,653 B2 * 12/2006 Abdel-Hadi ............. G01N 3/10
73/819
2018/0335494 A1 * 11/2018 Hakimuddin .......... G01R 33/46
2019/0204288 A1 * 7/2019 Zhang ...................... G01N 3/00

* cited by examiner

*Primary Examiner* — Brandi N Hopkins
(74) *Attorney, Agent, or Firm* — Bayramoglu Law Offices LLC

(57) ABSTRACT

A triaxial high temperature and high pressure rock mechanics load test platform includes a base, a lifting seat, and an intermediate connecting seat arranged between the base and the lifting seat. A hydraulic assembly is arranged between the base and the intermediate connecting seat; the intermediate connecting seat is connected with the lifting seat by means of a group of connecting rods; the lifting seat is enclosed by a side wall and a base plate to form a receiving groove with an upward opening; and a limiting device is arranged on the side wall of the lifting seat for preventing an MTS triaxial force sensor from disengaging from a support disk.

8 Claims, 2 Drawing Sheets

TRIAXIAL HIGH TEMPERATURE AND HIGH PRESSURE ROCK MECHANICS LOAD TEST PLATFORM

CROSS REFERENCE TO RELATED APPLICATIONS

This application is based upon and claims priority to Chinese Patent Application No. 201810403196.7, filed on Apr. 28, 2018 the entire contents of which are incorporated herein by reference.

TECHNICAL FIELD

The invention belongs to the field of rock mechanics test of engineering rock masses, and is intended to address the alignment and safety challenges in the dismounting and installation of high temperature and high pressure load sensors used in the existing mechanics test systems (MTS).

BACKGROUND

Deep earth engineering rock masses are in a complex stress state and environment including high temperature, high pressure, high seepage and dynamic load. For deep earth engineering construction, mechanical properties of the engineering rock masses in complex deep earth environments are necessary to provide basis and fundamental data for engineering construction and safe operation. At present, the MTS rock mechanics test system manufactured by US MTS is one of the most advanced and most commonly used rock mechanics test equipment in the world. The system is capable of simulating certain rock mechanics responses under complex deep earth conditions. In order to ensure accurate and reliable rock mechanics response simulation in a complex deep earth environment, one of the key factors lies in a high temperature and high pressure load sensor, a core component for measurement and control of high temperature and high pressure features. The high temperature and high pressure load sensor is disposed in a cavity of a high temperature and high pressure chamber with a narrow space and a special structure, and the load sensor is above a high temperature and high pressure base disposed with a series of leads for high temperature and high pressure load, deformation, temperature, hydraulic, seepage and ultrasound. The high temperature and high pressure sensor is inevitably subject to testing, maintenance and replacement before and after the rock mechanics simulation test in the complex deep earth environment. Currently, these operations are carried out manually. Dismounting and installation of a high temperature and high pressure load sensor with high mass from/in a narrow high temperature and high pressure cavity is rather tough even several people work together. Improper dismounting and installation may result in accidental fall of the load sensor, which may cause severe physical damage to the load sensor, mechanical damage to precise wires on the high temperature and high pressure base and serious personal injuries to installers. Due to the limited lifting strength and lifting time of manual operations and poor stability of manual lifting, the manual operations are extremely difficult and risky. This is a big difficulty and challenge in the rock mechanics tests in the deep earth environment. At present, effective solution or equipment are not available to solve the problem.

SUMMARY

The present invention aims to solve the technical problem by providing a triaxial high temperature and high pressure rock mechanics load test platform with the existing MTS test equipment.

The technical solution applied in the invention is a triaxial high temperature and high pressure rock mechanics load test platform, comprising a base, a lifting seat, and an intermediate connecting seat arranged between the base and the lifting seat; a hydraulic assembly is arranged between the base and the intermediate connecting seat; and a piston end of the hydraulic assembly is connected with a bottom of the intermediate connecting seat, and the other end thereof is connected with the base.

The intermediate connecting seat is connected with the lifting seat by means of a group of connecting rods.

The lifting seat consists of a base plate and a side wall arranged on the base plate; the base plate and the side wall are enclosed to form a receiving groove with an upward opening for housing a MTS high temperature and high pressure sensor; an operating channel running through the base plate is arranged at a center of the base plate of the lifting seat along an axial direction thereof; and a limiting device is arranged on the side wall of the lifting seat for preventing the MTS high temperature and high pressure sensor from disengaging from a support disk.

A through hole fitting a central alignment pin of an MTS hydraulic servo table is arranged on the base.

Further, the limiting device comprises a group of stop screws disposed uniformly around the side wall of the lifting seat. The stop screws pass through the side wall of the lifting seat along a radial direction of the lifting seat and are in threaded connection with the lifting seat.

Further, the piston end of the hydraulic cylinder is connected to a center of the intermediate connecting seat.

Further, an elbowed support member is arranged at both sides of the hydraulic assembly respectively; the two elbowed support members are symmetrical about a center line of a hydraulic cylinder; one end of the elbowed support member is hinged with the base, and the other end thereof is hinged with the intermediate connecting seat; and the elbowed support members are hinged by two transmission rods.

Further, the two elbowed support members are enclosed to form a parallelogram structure.

Further, the hydraulic assembly comprises a support seat and the hydraulic cylinder; the support seat is provided with a cavity running through the bottom thereof along the axial direction thereof and a through hole along the axial direction thereof from the cavity to a top end of the support seat, and the cavity is coaxial with the through hole; and a cylinder body of the hydraulic cylinder is arranged in the cavity, and a piston rod thereof is connected with the bottom of the intermediate connecting seat by the through hole.

Further, the support seat is configured as a circular truncated cone.

The invention has the following beneficial effects: the bearing system is time-saving and energy-saving in dismounting and installation of the load sensor compared with the manual operations; the bearing system is capable of providing stable and powerful support for the load sensor and applying a certain pulling force to the load sensor after the load sensor is locked in position by the limiting device, thus overcoming the difficulty of dismounting the load sensor in the presence of oil suction; the bearing system is capable of implementing steady lifting by the hydraulic assembly, avoiding damage of the sensor caused by vibration and other factors; the reliable limiting structure is capable of preventing the load sensor from fall and damage in case of accidents; and the bearing system is capable of implementing large-travel lifting of the load sensor easily by virtue of MTS lifting and loading systems.

DESCRIPTION OF THE PREFERRED EMBODIMENTS

Figure 1:
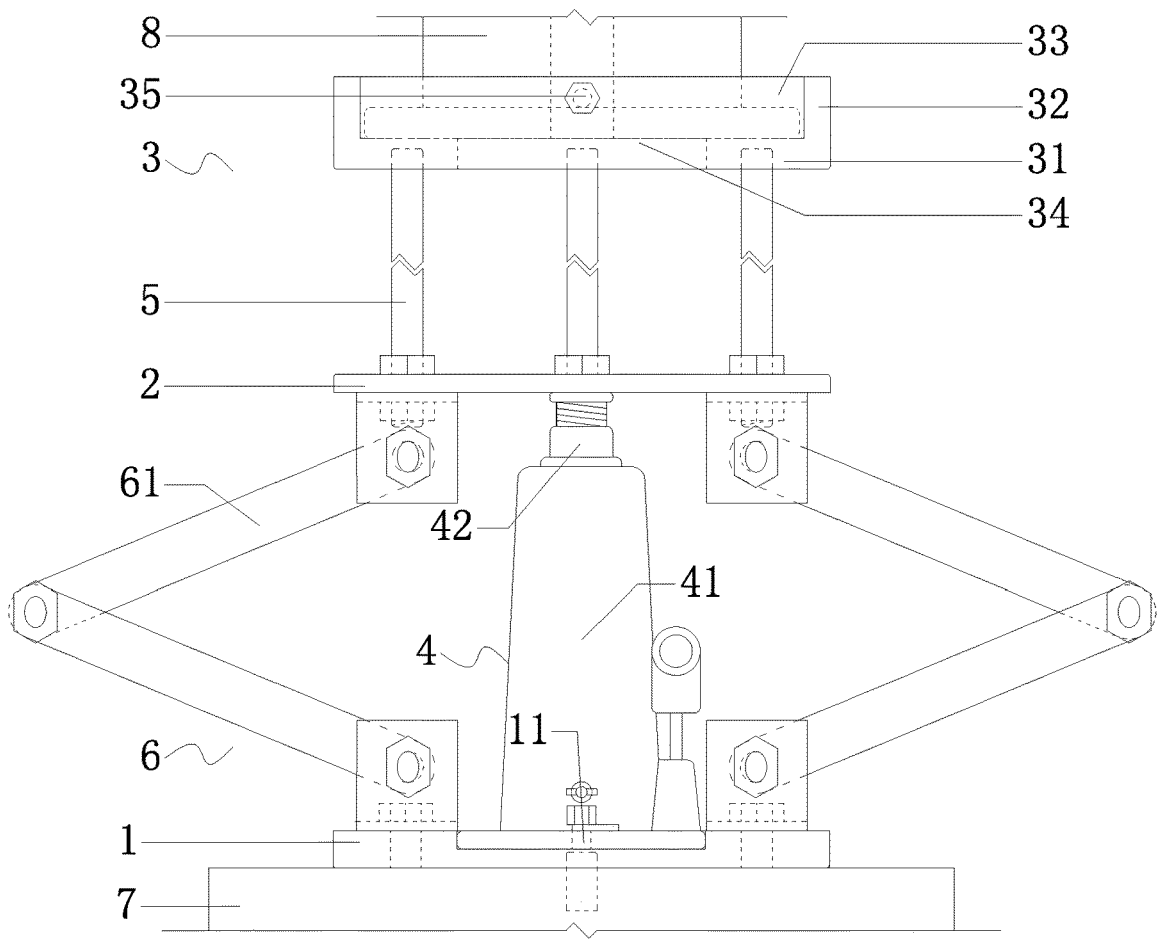
FIG. 1 is a structural diagram of the invention.

The invention will be further described in combination with drawings and embodiments:

As shown in FIG. 1, a triaxial high temperature and high pressure rock mechanics load test platform comprises a base 1, a lifting seat 3, and an intermediate connecting seat 2 arranged between the base 1 and the lifting seat 3; a hydraulic assembly 4 is arranged between the base 1 and the intermediate connecting seat 2; a piston end of the hydraulic assembly 4 is connected with a bottom of the intermediate connecting seat 2, and the other end thereof is connected with the base 1; the intermediate connecting seat 2 is connected with the lifting seat 3 by means of a group of connecting rods 5; the lifting seat 3 comprises a base plate 31 and a side wall 32 arranged on the base plate 31; the side wall 32 and the base plate 31 are enclosed to form a receiving groove 33 with an upward opening for housing an MTS high temperature and high pressure sensor; an operating channel 34 running through the base plate 31 is arranged at a center of the base plate 31 of the lifting seat 3 along an axial direction thereof; a limiting device is arranged on the side wall 32 of the lifting seat 3 for preventing the MTS high temperature and high pressure sensor from disengaging from a support disk; and a though hole 11 fitting a central alignment pin of an MTS hydraulic servo table 7 is arranged on the base 1.

In the invention, the lifting seat 3 is used for lifting a load sensor 8 and supported on the intermediate connecting seat 2. The intermediate connecting seat 2 is supported on a top end of the hydraulic assembly 4. The load sensor is lifted to a mounting position by jacking up the lifting seat 3 through extension of a piston rod of the hydraulic assembly 4, or the load sensor is removed from a rigid column in a triaxial chamber by pulling back the lifting seat 3 through retraction of the piston rod of the hydraulic assembly 4. The side wall 32 and the base plate 31 of the lifting base 3 are enclosed to form a receiving groove 33 with an upward opening for housing the load sensor 8. The load sensor 8 is axially limited by the side wall 32, bottom limited by the base plate 31, and locked by the limiting device to prevent the load sensor 8 from moving in the receiving groove 33. An operating channel 34 runs through the base plate 31 to enable operators to install and dismount bolts through the operating channel 34 below, thus avoiding the risk of working at heights.

The bearing system is time-saving and energy-saving in dismounting and installation of the load sensor compared with manual operations; the bearing system is capable of providing stable and powerful support for the load sensor and applying a certain pulling force to the load sensor 8 after the sensor is locked in position by the limiting device, thus overcoming the difficulty of dismounting the load sensor in the presence of oil suction; the bearing system is capable of implementing steady lifting by the hydraulic assembly 4, avoiding damage of the sensor caused by vibration and other factors; and the reliable limiting structure is capable of preventing the load sensor from fall and damage in case of accidents.

Figure 2:
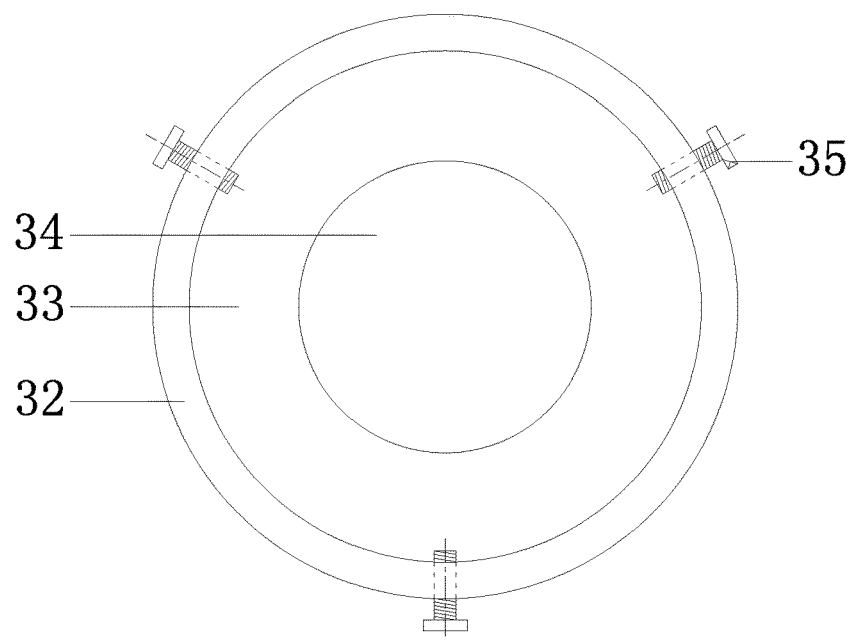
FIG. 2 is a top view of the lifting seat.

Preferably, as shown in FIGS. 1 and 2, the limiting device comprises a group of stop screws 35 disposed uniformly around the side wall 32 of the lifting seat 3. The stop screws 35 pass through the side wall 32 of the lifting seat 3 along the radial direction of the lifting seat 3 and are in threaded connection with the lifting seat 3.

Preferably, the piston end of the hydraulic assembly 4 is connected to the center of the intermediate connecting seat 2 to maintain levelness of the intermediate connecting seat 2 and the lifting seat 3 so as to avoid titling of the load sensor 8.

Certainly, the intermediate connecting seat 2 is capable of being supported solely by the hydraulic assembly 4; but lack of sufficient support points is not conductive to supporting stability. Therefore, an elbowed support member 6 is arranged at both sides of the hydraulic assembly 4 preferably; the two elbowed support members 6 are symmetrical about a center line of a hydraulic cylinder 42; one end of the elbowed support member 6 is hinged with the base 1, and the other end thereof is hinged with the intermediate connecting seat 2; and the elbowed support members 6 are hinged by two transmission rods 61. The hydraulic cylinder 42 and the elbowed support members 6 are capable of providing strong support and high stability.

The two elbowed support members 6 is capable of being arranged in an X shape; but the elbowed support members 6 are pressed in the direction of the hydraulic assembly 4 at compression, which is prone to causing interference and shortening the compression distance. Therefore, the two elbowed support members 6 are preferably enclosed to form a parallelogram structure.

Figure 3:
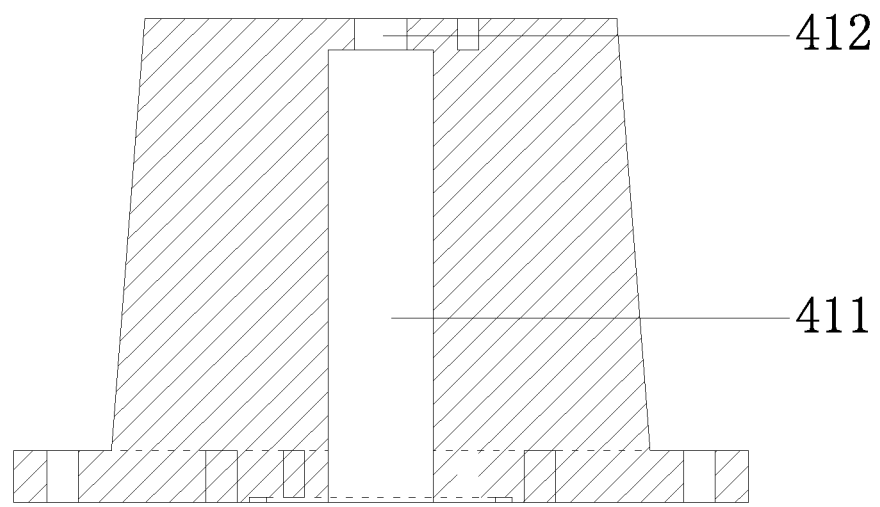
FIG. 3 is a sectional view of the support seat;
Marks in the figures: base 1, through hole 11, intermediate connecting seat 2, lifting seat 3, base plate 31, side wall 32, receiving groove 33, operating channel 34, stop screw 35, hydraulic assembly 4, support seat 41, cavity 411, through hole 412, hydraulic cylinder 42, connecting rod 5, elbowed support member 6, transmission rod 61, MTS hydraulic serve table 7, and load sensor 8.

The hydraulic assembly 4 is capable of solely comprising a hydraulic cylinder. However, preferably, in order to increase rigidity of the hydraulic cylinder, the hydraulic assembly 4 comprises a support seat 41 and a hydraulic cylinder 42, as shown in FIGS. 2 and 3; the support seat 41 is provided with a cavity 411 running through the bottom along the axial direction and a through hole 412 along an axial direction from a cavity 411 to a top end of the support seat 41, and the cavity 411 is coaxial with the through hole 412; a cylinder body of the hydraulic cylinder 41 is arranged in the cavity 411, and a piston rod passes through the through hole 412 and is connected with the bottom of the intermediate connecting seat 2. Extension and retraction of the piston rod is adjusted via the through hole 412, thus improving movement stability and preventing tilting of the intermediate connecting seat 2 and the lifting seat 3 thereon. In addition, there are additional support points for the piston rod, which improves rigidity and expands service life.

Preferably, the support seat 41 is configured as a circular truncated cone.

What is claimed is:

1. A triaxial high temperature and high pressure rock mechanics load test platform comprising a base, a lifting seat, and an intermediate connecting seat arranged between the base and the lifting seat;

wherein, a hydraulic assembly is arranged between the base and the intermediate connecting seat, a piston end of the hydraulic assembly is connected with a bottom of the intermediate connecting seat, and the other end of the hydraulic assembly is connected with the base, the intermediate connecting seat is connected with the lifting seat by means of a group of connecting rods;

the lifting seat comprises a base plate and a side wall arranged on the base plate, the base plate and the side wall are enclosed to form a receiving groove with an upward opening for housing a MTS high temperature and high pressure sensor, an operating channel running through the base plate is arranged at a center of the base plate of the lifting seat along an axial direction of the base plate, and a limiting device is arranged on the side wall of the lifting seat for preventing the MTS high temperature and high pressure sensor from disengaging from a support disk; and a through hole fitting a central alignment pin of an MTS hydraulic servo table is arranged on the base.

2. The triaxial high temperature and high pressure rock mechanics load test platform of claim 1, wherein, the limiting device comprises a group of stop screws disposed uniformly around the side wall of the lifting seat, the group of stop screws pass through the side wall of the lifting seat along a radial direction of the lifting seat and are in a threaded connection with the lifting seat.

3. The triaxial high temperature and high pressure rock mechanics load test platform of claim 1, wherein, the piston end of the hydraulic cylinder is connected to a center of the intermediate connecting seat.

4. The triaxial high temperature and high pressure rock mechanics load test platform of claim 1, wherein, two elbowed support members are arranged at both sides of the hydraulic assembly respectively; the two elbowed support members are symmetrical about a center line of a hydraulic cylinder;

a first end of each of the two elbowed support members is hinged with the base, and second end of each of the two elbowed support members is hinged with the intermediate connecting seat; and the two elbowed support members are hinged by two transmission rods.

5. The triaxial high temperature and high pressure rock mechanics load test platform of claim 1, wherein, the two elbowed support members are enclosed to form a parallelogram structure.

6. The triaxial high temperature and high pressure rock mechanics load test platform of claim 1, wherein, the hydraulic assembly comprises a support seat and the hydraulic cylinder;

the support seat is provided with a cavity running through a bottom of the support seat along an axial direction of the support seat and a through hole along the axial direction of the support seat from the cavity to a top end of the support seat, and the cavity is coaxial with the through hole; and a cylinder body of the hydraulic cylinder is arranged in the cavity, and a piston rod of the cylinder body is connected with the bottom of the intermediate connecting seat by the through hole.

7. The triaxial high temperature and high pressure rock mechanics load test platform of claim 6, wherein, the support seat is configured as a circular truncated cone.

8. The triaxial high temperature and high pressure rock mechanics load test platform of claim 2, wherein, two elbowed support members are arranged at both sides of the hydraulic assembly respectively; the two elbowed support members are symmetrical about a center line of a hydraulic cylinder;

a first end of each of the two elbowed support members is hinged with the base, and second end of each of the two elbowed support members is hinged with the intermediate connecting seat; and the two elbowed support members are hinged by two transmission rods.

* * * * *